United States Patent
Spindler (10) Patent No.: US 10,441,221 B2
(45) Date of Patent: Oct. 15, 2019

(54) GRAFT PROSTHESIS WITH POCKET FOR MICROSYSTEM

(71) Applicant: COOK MEDICAL TECHNOLOGIES LLC, Bloomington, IN (US)

(72) Inventor: Ralf Spindler, Bloomington, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 71 days.

(21) Appl. No.: 15/633,179

(22) Filed: Jun. 26, 2017

(65) Prior Publication Data

US 2018/0368775 A1  Dec. 27, 2018

(51) Int. Cl.

| A61B 5/00 | (2006.01) |
|---|---|
| A61F 2/06 | (2013.01) |
| A61B 5/07 | (2006.01) |
| A61B 5/0215 | (2006.01) |
| A61F 2/07 | (2013.01) |
| A61B 5/021 | (2006.01) |
| A61B 5/026 | (2006.01) |
| A61B 5/145 | (2006.01) |

(52) U.S. Cl.
CPC .......... *A61B 5/6862* (2013.01); *A61B 5/0215* (2013.01); *A61B 5/076* (2013.01); *A61B 5/4851* (2013.01); *A61F 2/06* (2013.01); *A61F 2/07* (2013.01); *A61B 5/021* (2013.01); *A61B 5/026* (2013.01); *A61B 5/14532* (2013.01); *A61B 5/14542* (2013.01); *A61B 2560/0443* (2013.01); *A61B 2562/028* (2013.01); *A61F 2210/009* (2013.01); *A61F 2250/0002* (2013.01); *A61F 2250/0059* (2013.01)

(58) Field of Classification Search
USPC ..................................... 623/1.1–3.1; 600/486
See application file for complete search history.

(56) References Cited

U.S. PATENT DOCUMENTS

| 6,296,661 B1 | 10/2001 | Davila et al. |
|---|---|---|
| 6,517,570 B1 | 2/2003 | Lau et al. |
| 6,695,875 B2 | 2/2004 | Stelter et al. |
| 6,748,953 B2 | 6/2004 | Sherry et al. |

(Continued)

FOREIGN PATENT DOCUMENTS

| CN | 104931127 A | 9/2015 |
|---|---|---|
| EP | 1 545 393 B1 | 6/2005 |

(Continued)

OTHER PUBLICATIONS

YouTube Video, www.youtube.com/watch?v=DBa41wej-NE, published on Mar. 20, 2013 and retrieved on Jun. 22, 2017, 1 page.

(Continued)

*Primary Examiner* — Yashita Sharma
(74) *Attorney, Agent, or Firm* — Brinks Gilson & Lione (57) ABSTRACT

A medical device, such as a prosthesis, may include a graft material and a pocket disposed along at least one of luminal and abluminal surfaces of the graft material. The pocket may include a pocket opening leading into an enclosed cavity. The enclosed cavity may be sized to receive at least a portion of a microsystem, and the pocket may be accessible in vivo for removal of the microsystem from the pocket.

17 Claims, 6 Drawing Sheets

(56) References Cited

U.S. PATENT DOCUMENTS

| | | | |
|---|---|---|---|
| 6,840,956 B1 | 1/2005 | Wolinsky et al. | |
| 7,160,318 B2 | 1/2007 | Greenberg et al. | |
| 7,232,459 B2 | 6/2007 | Greenberg et al. | |
| 7,335,224 B2 | 2/2008 | Ohlenschlaeger | |
| 7,686,842 B2 | 3/2010 | Pavcnik et al. | |
| 7,722,657 B2 | 5/2010 | Hartley | |
| 7,914,572 B2 | 3/2011 | Hartley et al. | |
| 9,107,605 B2* | 8/2015 | Boyle | A61B 5/076 |
| 9,168,162 B2 | 10/2015 | Smouse | |
| 2002/0183628 A1* | 12/2002 | Reich | A61B 5/02014 |
| | | | 600/486 |
| 2005/0107866 A1 | 5/2005 | Brown et al. | |
| 2006/0129050 A1 | 6/2006 | Martinson et al. | |
| 2007/0191816 A1* | 8/2007 | Behan | A61F 2/88 |
| | | | 604/890.1 |
| 2007/0244373 A1* | 10/2007 | Osypka | A61B 5/0031 |
| | | | 600/301 |
| 2009/0036975 A1 | 2/2009 | Ward et al. | |
| 2015/0018933 A1 | 1/2015 | Yang et al. | |

FOREIGN PATENT DOCUMENTS

| | | |
|---|---|---|
| EP | 1 558 177 A2 | 8/2005 |
| EP | 2 586 404 A1 | 5/2013 |
| WO | WO 01/87137 | 11/2001 |
| WO | WO 2004/019819 A1 | 3/2004 |
| WO | WO 2004/037116 A2 | 5/2004 |
| WO | WO 2013/074921 A2 | 5/2013 |

OTHER PUBLICATIONS

Extended European Search Report for 18275089.3 dated Oct. 18, 2018, 7 pgs.

* cited by examiner

GRAFT PROSTHESIS WITH POCKET FOR MICROSYSTEM

BACKGROUND

The present disclosure relates generally to medical devices, and particularly, to endoluminal prostheses, stent-grafts, or grafts with a pocket for a removable microsystem and methods for the manufacture and use of the same for repair of damaged vessels, ducts, or other physiological pathways.

Various interventions have been provided for weakened, aneurysmal, dissected or ruptured vessels, including surgical interventions and endovascular interventions. Endovascular interventions generally include inserting an endoluminal device or prosthesis such as a stent or stent graft into the damaged or diseased body lumen to provide support for the lumen, and to exclude damaged portions thereof. Such prosthetic devices are typically positioned at the point of treatment or target site by navigation through the vessel, and possibly other connected branch vessels, until the point of treatment is reached. This navigation may require the device to be able to move axially through the vessel(s) prior to deployment, while still maintaining the ability to exert an outward force on the interior wall once deployed.

In the field of aortic interventions, endoluminal devices are placed in vessels to address and correct diseased tissue resulting from atherosclerotic plaques, aneurysm or weakening of body vessel walls, and arterial dissection. In the case of atherosclerosis, plaque buildup results in narrowing of the vessel, which may lead to reduced or blocked blood flow within the body vessel. Endoluminal devices for atherosclerosis act to radially expand the narrowed area of the body vessel to restore normal blood flow. In the case of an aneurysm, a weakening of the body vessel wall results in ballooning of the body vessel, which can eventually lead to rupture and subsequent blood loss. In some cases, the aneurysmal sac may include plaque. Endoluminal devices for aneurysms act to seal off the weakened area of the body vessel to reduce the likelihood of the body vessel rupture. In the case of arterial dissection, a section of the innermost layer of the arterial wall is torn or damaged, allowing blood to enter false lumen divided by the flap between the inner and outer layers of the body vessel. The growth of the false lumen may eventually lead to complete occlusion of the actual artery lumen. Endoluminal devices for dissection healing would reappose the dissection flap against the body vessel wall to close it off and restore blood flow through the true lumen.

Medical imaging methods like fluoroscopy and MRI are commonly used to visualize the correct prosthesis position in vivo and to check the current status of the aneurysm, for example, to check for endoleaks. What is needed is an implantable prosthesis to collect data and monitor physiological status of the patient.

SUMMARY

Medical devices with one or more pocket configure to receive one or more microsystems are described herein. In one example, a medical device includes a tubular graft material having an abluminal surface and a luminal surface. A pocket may be disposed along at least one of the luminal and abluminal surfaces of the graft material. The pocket may include a pocket opening leading into an enclosed cavity. The enclosed cavity may be sized to receive at least a portion of a microsystem, and the pocket may be accessible in vivo for removal of the microsystem from the pocket.

In another example, a medical device includes a tubular graft material having an abluminal surface and a luminal surface. A pocket may be disposed along the luminal surface of the graft material, includes an opening leading into an enclosed cavity. A portion of the graft material may include a magnet to removably couple to a microsystem when received within the enclosed cavity. The pocket may be accessible in vivo for removal of the microsystem from the pocket.

In another example, an implantable medical device may include a tubular graft material having an outer layer and an inner layer. A pocket may include a pocket opening formed in the inner layer leading into a pocket cavity defined at least partially by the outer layer and the inner layer. The pocket cavity may be sized to receive at least a portion of a microsystem. The pocket may include a reinforced pivotable lid.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

Medical devices for implantation within a human or animal body for repair of damaged vessels, ducts, or other physiological pathways are provided. The medical devices have a graft covering with a pocket configured to retain a microsystem. The microsystem may be utilized to collect information about the physiological status of a patient and/or status about the implanted medical device. The pocket of the medical device may embed, attach, or hold a microsystem. The pocket may be configured to facilitate removal of the existing microsystem and to permit receipt of a subsequent microsystem. The subsequent microsystem may be the same existing microsystem or a different microsystem.

In the present application, the term "proximal end" is used when referring to that end of a medical device closest to the heart after placement in the human body of the patient, and may also be referred to as inflow end (the end that receives fluid first), and the term "distal end" is used when referring to that end opposite the proximal end, or the one farther from the heart after its placement, and may also be referred to as the outflow end (that end from which fluid exits).

Medical devices may include any device that is introduced temporarily or permanently into the body for the prophylaxis or therapy of a medical condition. For example, such medical devices may include, but are not limited to; endovascular grafts, stent grafts, bifurcated stent grafts or assembly of a multicomponent prosthesis, meshes, vascular grafts, stent-graft composites, filters (for example, vena cava filters), vascular implants, tissue scaffolds, myocardial plugs, valves (for example, venous valves), various types of dressings, endoluminal prostheses, vascular supports, or other known biocompatible devices.

Figure 1:
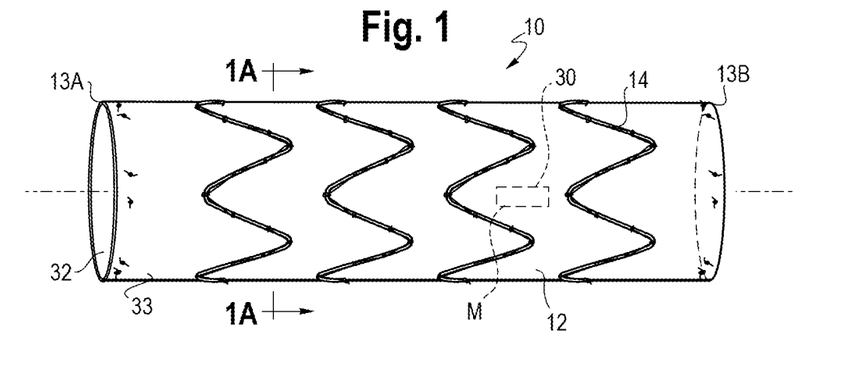
FIG. 1 is a perspective view of an example of a medical device including a pocket housing a microsystem.

Now looking more closely at the drawings, FIG. 1 depicts one example of a medical device 10 including a tubular graft covering 12. The graft covering 12 may be cylindrical having a nominal expanded diameter along the entire longitudinal length of the medical device. The graft covering includes a distal end 13A and a proximal end 13B. It is contemplated the graft covering 12 may have segments that are tapered. In one example, the medical device 10 is suitable for placement into an aorta for engaging against the aortic walls. The medical device 10 may also include a stent frame structure 14 disposed along the graft covering 12. The graft covering 12 may be attached to the stent frame structure 14 by stitching and/or bonding. The graft covering 12 include one or more pockets 30.

Figure 1A:
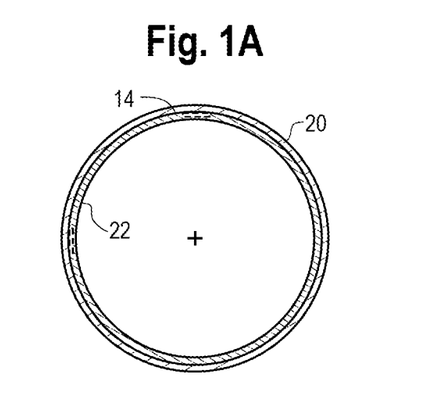
FIG. 1A is a radial cross-sectional view of the medical device in FIG. 1 taken along the lines 1A-1A.

The graft covering 12 may include a single layer or multiple layers, such as, for example, a first layer, a second layer, or a combination of both. In one example, the first layer 20 is an outer graft layer coaxially disposed over the second, inner graft layer 22. When employed, the stent frame structure 14 may be disposed between the first and second layers 20, 22.

The stent frame structure 14 may be any device or structure that provides or is configured to provide rigidity, expansion force, or support to a body part, for example, a diseased, damaged, or otherwise compromised body lumen. The stent frame structure 14 may include a single stent structure or a plurality of stents. Stent frame structure may expand by virtue of its own resilience (i.e., self-expanding), upon the application of an external force (i.e., balloon-expandable), or by a combination of both.

Figure 2:
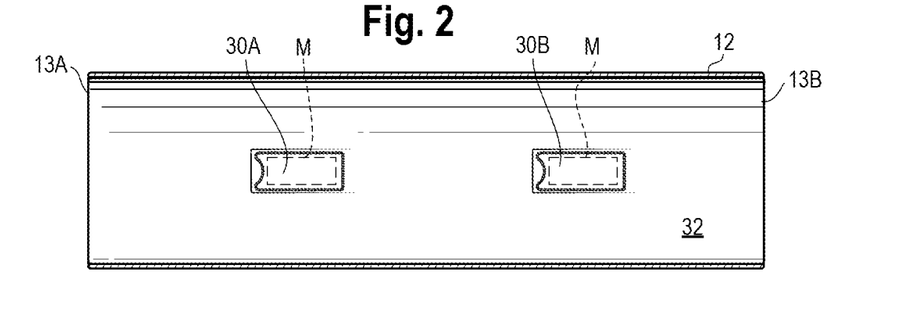
FIG. 2 is an axial cross-sectional view of another example of a medical device including a plurality of pockets with microsystems, viewed from the inside.

The graft covering 12 may include one or more pockets 30. FIG. 2 illustrates a luminal surface 32 of the graft covering 12 including a first pocket 30A and a second pocket 30B longitudinally upstream from the first pocket 30A in the proximal direction. The first pocket 30A is closer to the distal end of the graft covering than the proximal end of the graft covering. In one example, only one of the first and second pockets 30A, 30B is provided. In another example, the first and second pockets 30A, 30B are circumferentially disposed from one another along the same annular segment. In another example, the first and second pockets 30A, 30B are circumferentially and longitudinally disposed from one another in an offsetting pattern. In another example, additional pockets are circumferentially and/or longitudinally disposed from the first and second pockets.

A microsystem M may be disposed within the one or more pockets 30 or other pocket configurations described herein. In one example, more than one microsystem may be fit within a single pocket. The microsystem M includes microfluidic and/or microelectronic chips (including nanostructures) having one or more sensors that are configured to collect information about the physiological status of a patient, such as the physiological blood parameters, such as, for example, blood pressure, flow, oxygen level, sugar level, or other factors. In one example, the microsystem M is a micro-electro-mechanical systems (MEMS) sensor. The MEMS sensor includes mechanical elements, sensors, actuators and electronics on a common silicon substrate on a chip. Various microsystem may be utilized herein, including for example fluid pressure sensors (sac pressure and aortic blood pressure), contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors, temperature sensors, and the like. Parameters of the medical device may also be monitored, such as, for example, the graft wall tension, the graft position, the graft diameter, and/or the rate of biodegradation of the stents. The microsystem may be wireless or connected to a wireless microprocessor. The microsystem may require a power supply or may be passive and not requiring its own power supply.

The microsystem M may include a microprocessor for the controller, a memory, an I/O circuit to interface with any sensors, and a power supply, as well as antennas (transmitter and/or receivers) for sending and receiving the data. Microprocessors may be programmed to collect data from the various sensors on any desired schedule as set by the medical professional and for receiving updates in software and firmware updates. All activity may be continuously monitored post operation or post-procedure and the data collected and stored in the memory of the microsystem. The microsystem may be configured to output data to a computer or other device for display and use by the physician to treat the patient. The electronic communication is wireless, using known protocols, to another processor or computer via a wired/wireless services entity, a telephone system, network system, Voice over IP system, internet and cable access (e.g., an Internet Service Provider), and/or satellite systems such as HughesNet and VSAT Systems. The power supply is configured to provide an electrical current to components of the microsystem, such as sensors and antennas. The power supply may be configured to create a piezoelectrical current from a movement of fluid through the medical device, a pulsatile movement of medical device, and/or an application of any suitable material to create a piezoelectrical current. The power supply may include a radio frequency (RF) induction coil (such as, for example, a planar coil, a spiral coil, a spiral coil having a 'z' configuration, or a vertical coil configuration) operatively coupled to microsystem components. Microsystem M may include an inductor electronically coupled to a capacitor and a ground plane that is electronically coupled to each sensor or power component. An external power source may be provided outside the patient's body for charging and/or powering the microsystem M. For example, the external power source includes an oscillator electronically coupled to an amplifier and an inductor. During operation, a magnetic coupling between the microsystem's inductor and the external power source's inductor to generate an alternating current that is channeled to and powers the microsystem components, such as, for example, sensors, microprocessor, and/or antennas.

One example microsystem M is available from Ecole Polytechnique Federale de Lausanne (EPFL) of Switzerland. The EPFL microsystem is a 14 mm device and configured to provide one or more indicators from the blood (proteins, glucose, lactate, ATP, and others). The EPFL device includes a communication module, for example, for Bluetooth, to transmit data from the processor to an external device, such as a computer or phone, for tracking.

Figure 3:
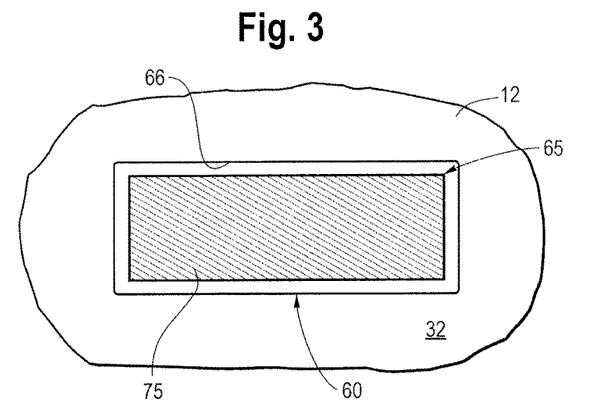
FIG. 3 depicts an example of a pocket configuration for a medical device, viewed from the inside.
Figure 4:
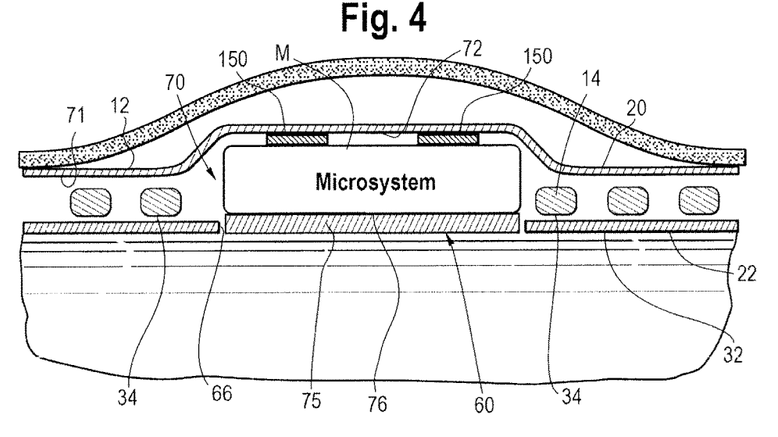
FIG. 4 is a magnified cross-sectional partial view of the pocket configuration in FIG. 3, with the medial device implanted within a body vessel.

FIGS. 3-4 illustrate one exemplary configuration of a pocket (now referred to as pocket 60) along the luminal surface 32 of the graft covering 12. The pocket 60 is shown disposed between adjacent stent members 34 of the stent frame structure 14 to minimize the profile of the medical device. A pocket opening 65 may be formed into the inner layer 22 by pocket edges 66 leading into a pocket interior cavity 70, such that the pocket opening 65 and the pocket cavity 70 is sized to receive the microsystem M. The pocket cavity 70 may be enclosed from within such that the opening of the lid is the primary way to access the pocket. The pocket opening 65 overlaps the inner surface 71 of the outer layer 20 to define a pocket base 72. A cover material 75 may be applied to the luminal side 76 of the microsystem M. The cover material 75 has a sidewall thickness sized to fill the relative void thickness such that the luminal surface 32 of the medical device is more continuous to promote laminar flow. The cover material 75 may include ends that overlap the pocket edges 66 to minimize leakage into the medical device.

Figure 5:
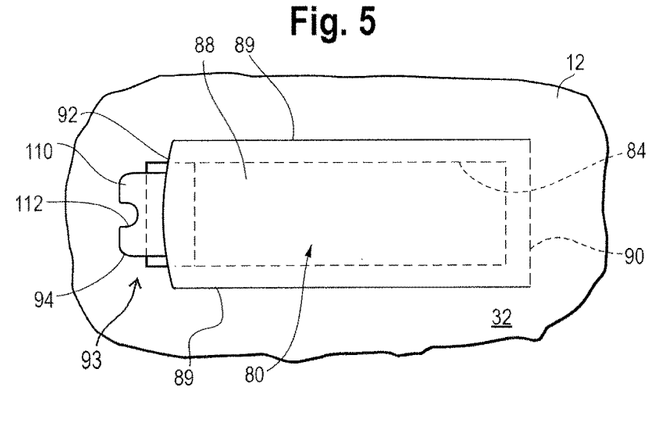
FIG. 5 depicts another example of a pocket configuration for a medical device, viewed from the inside.
Figure 6:
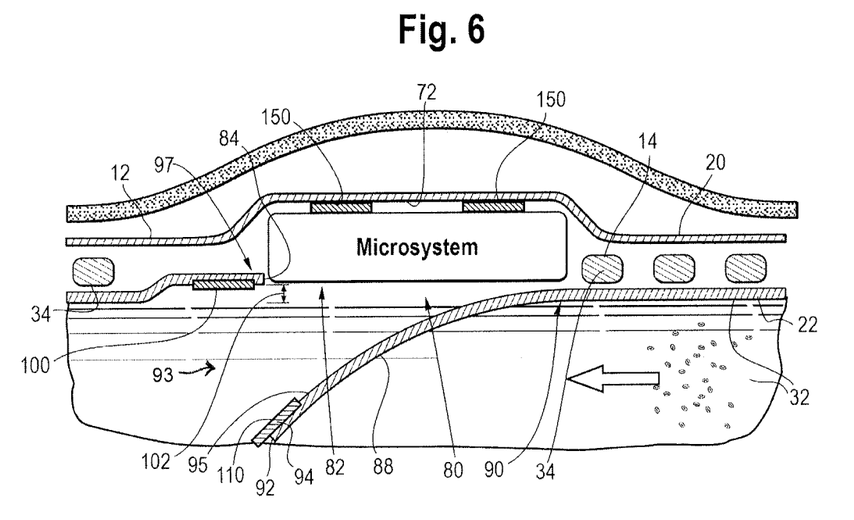
FIG. 6 is a magnified cross-sectional partial view of the pocket configuration in FIG. 5, with the medial device implanted within a body vessel.

FIGS. 5-6 illustrate another exemplary configuration of a pocket (now referred to as pocket 80) along the luminal surface 32 of the graft covering 12. The pocket 80 is shown disposed between stent members 34 of the stent frame structure 14 to minimize the profile of the medical device. The pocket opening 82 is formed into the inner layer 22 by pocket rim edges 84, such that the pocket opening 82 is sized to receive the microsystem M. The pocket 80 includes a lid 88 sized to cover at least partially the pocket opening 82. In one example, the lid 88 is sized to cover the entire pocket opening 82 and the lid edges 89 overlap the pocket edges 84. The lid 88 includes a base 90 coupled to the luminal surface 32 and a tip 92. The lid 88 is pivotably coupled to the luminal surface at the base 90. In one example, the lid 88 is as an extension of a common piece of graft material of the inner layer 22. In another example, the lid 88 may be made from a separate piece of graft material that is sewn or otherwise attached to the inner layer.

The lid tip 92 may be removably attached to the luminal surface 32. In this manner, the lid 88 is movable between an open configuration (FIG. 6) and a closed configuration (FIG. 5). The lid and the rim edges of the pocket may have complementarily coupling devices 93 for attachment and detachment. The coupling devices may include, such as, for example, magnets, hook-and-loop fasteners (Velcro™), button-and-slot fastening, press-in-snap fasteners, or button and loop fasteners. In other examples, the lid and the rim edges of the pocket may be coupled to one another for attachment and detachment via a string system forming a loop along one of the lid and the rim edges of the pocket and a trigger wire or string along the other that is insertable into the loop. In one example, the lip tip 92 includes one or lid magnets 94 securely fixed to an inner surface 95 of the lid 88. The tip end 97 of the pocket rim edges 84 includes one or rim magnets 100 securely fixed to the luminal surface 32 of the inner layer. The lid and rim magnets 94, 100 may be sewn along their respective graft surfaces, clipped, riveted, or stapled to the graft surfaces, bonded with an adhesive, or otherwise fixedly secured. The lid and rim magnets 94, 100 may be coupled differently than one another. The lid magnets 94 are magnetically attracted to the rim magnets 100 for magnetically coupling to the one another. In this matter, the microsystem M may be removed from the pocket 80 when the pocket is in the open configuration, as will be described. The lid and rim magnets 94, 100 may not need to be very strong as blood pressure within the lumen of the medical device will assist in holding the lid 88 closed over the pocket opening 82.

The tip end 97 of the pocket rim edge 84 with the rim magnets 100 securely fixed may be recessed from the remaining luminal surface by the depth 102 of at least the thickness of the rim magnet 100. In one example, the inset depth 102 may accommodate the rim magnet thickness and the thickness of the lid magnet 94 such that the luminal surface 32 of the medical device is a more continuous surface to promote laminar flow.

As show in FIG. 5, an extended portion 110 of the lid magnet 94 may extend beyond the lid edge 89. The extended portion 110 may provide a landing target for a grasper device, as will be described, to be used to decouple the lid magnet 94 from the rim magnet 100 to move the lid 88 to the open configuration. The extended portion 110 may include a grasping feature 112 accessible outside the lid. The grasping feature 112 may include a radial lip, an indentation, an opening, or a slot (as shown) configured for mechanical engagement with the grasper device.

Figure 7:
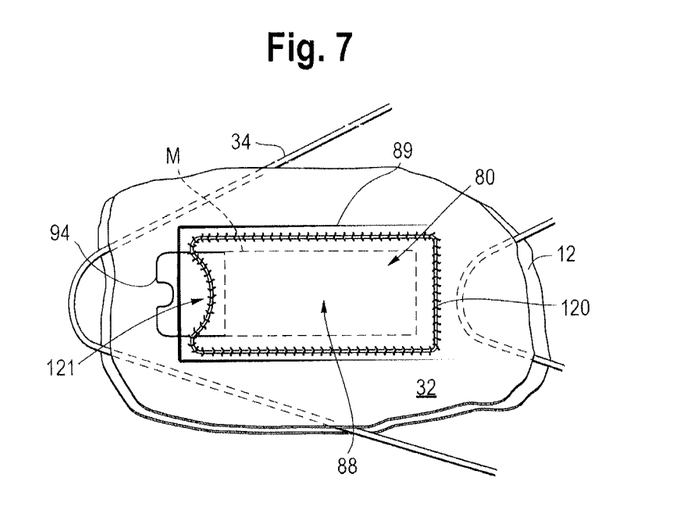
FIG. 7 depicts another example of a pocket configuration for a medical device with a reinforced lid, viewed from the inside.

Any of the lids disclosed herein may include a reinforcement band 120. The band 120 may be stitched or otherwise attached to the lid 88, as shown in FIG. 7. The reinforcement band 120 may assist with holding the lid 88 in either closed or open configurations. The reinforcement band 120 may add structural support to the lid 88 to ensure the reinforced lid remains over the pocket opening. For example, when the lid 88 pivots open as described later, the reinforcement band 120 may be arranged on the lid to prevent collapsing of the lid in an accordion fashion when using the grasper to open the lid. The reinforcement band 120 may be disposed along a single side, two sides, three sides, or the entire perimeter (as shown) of the lid edge 89, and/or across the intermediate of the lid. The band 120 may comprise a single element or a plurality of elements. The reinforcement band may include a grasping feature 121. The grasping feature 121 may include a radial lip or an indentation configured for mechanical engagement with the grasper device.

The reinforcement band may also be activatable to move between the open and closed configurations. For example, the band may be made for shape memory material. The shape memory material may be at least one of a metal, a metal alloy, a nickel titanium alloy, and a shape memory polymer. Shape memory materials have the desirable property of becoming rigid, that is, returning to a remembered state, when heated above a transition temperature. A shape memory alloy suitable for the present invention is Ni—Ti available under the more commonly known name Nitinol.

When this material is heated above the transition temperature, the material undergoes a phase transformation from martensite to austenite, such that material returns to its remembered state. The heat of the band may be activated inductively by an external inductive source, activated optically by a light source, or other means known in the art.

Figure 8:
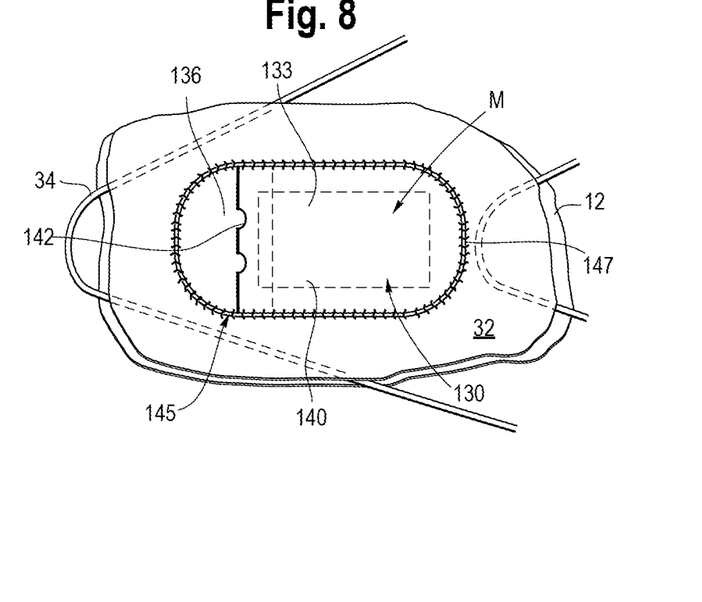
FIG. 8 depicts another example of a pocket configuration for a medical device, viewed from the inside.
Figure 9:
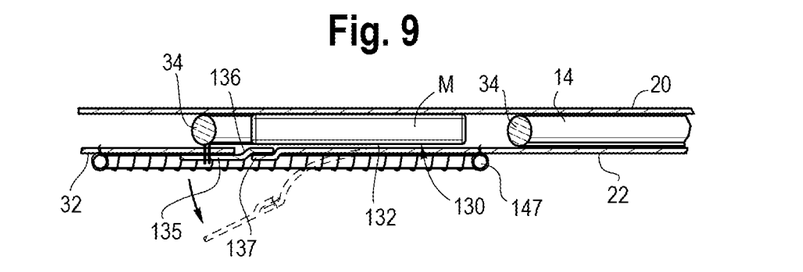
FIG. 9 is a magnified cross-sectional partial view of the pocket configuration in FIG. 8.

FIGS. 8-9 illustrate another exemplary configuration of a pocket (now referred to as pocket 130) along the luminal surface 32 of the graft covering 12. The pocket 130 is shown disposed between stent members 34 of the stent frame structure 14 to minimize the profile of the medical device. The pocket opening 132 is formed with the inner layer 22 defining a first flap 133 and a second graft material piece 135 defining a second flap 136 overlapping the first flap 133 along an overlapped edge 140. Separation of the first and second flaps 133, 136 along the overlapped edge 140 is sized to create the pocket opening 132 sized to receive the microsystem M. The second piece 135 is coupled to the inner layer 22, such as, for example, by stitching or bonding. In one example, the first flap may comprise a graft material piece that is coupled to the inner layer 22, such as, for example, by stitching or bonding. The combined size of the flaps 133, 136 is sized to cover the microsystem. The stitching of the flaps extends around part of the flaps but leave a central portion not stitched so the flaps can be opened back to allow access through the pocket opening.

The first flap 133 includes several grasping features 142. The grasping feature 141 may include a radial lip, an indentation, an opening, or a slot formed in the edge of the first flap (as shown) configured for mechanical engagement with the grasping device. The grasping feature may protrude from the inner layer. The protruding grasping feature may allow a point of purchase for a grasper to enable to engage against the first flap and to allow access within the pocket.

The pocket edges of any of the pocket configurations described herein may be stitched and/or reinforced to reinforce the pocket edges and inhibit tearing from the pocket edges. In one example shown in FIG. 8, the pocket edges 145 may be stitched. In another example, the pocket edges 145 may include a reinforcement edge band 147 stitched or otherwise attached along the pockets edges 145 that define the pocket opening. In one example, a combination of the reinforcement band 120 and the reinforcement edge band 147 may be used.

In any one of the described examples, the microsystem M may be securely coupled to the pocket base, such as the pocket base 72 in FIGS. 4 and 6, such as by bonding with an adhesive, magnetic coupling, or other attachment means. The pocket base 72 is the overlapped region defined where the opening overlaps the inner surface of the outer layer. In one example, the pocket base 72 includes one or magnets 150 securely fixed to the inner surface 71 of the outer layer 20. The magnet 150 may be sewn along the inner surface 71, clipped, riveted, or stapled to the inner surface 71, bonded with an adhesive, or otherwise fixedly secured to the inner surface 71. The microsystem M has magnetism capable of magnetically coupling to the one or more magnets 150. In this matter, the microsystem M may be removed from the magnets, as will be described.

Figure 10:
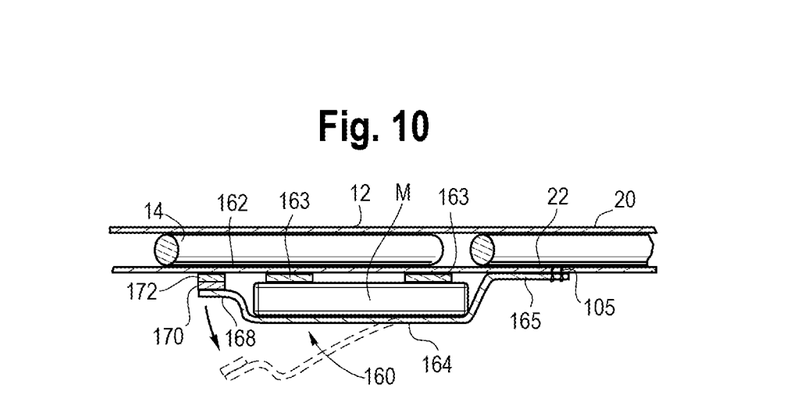
FIG. 10 is a magnified cross-sectional partial view of another example of a pocket configuration for a medical device.

Any of the described pocket configuration may be premade prior to attachment to the inner layer so as to not compromise the inner layer. Pieces of graft material may be sized and attached to one another, such as by stitching, in order to form the pocket. FIG. 10 illustrates such configuration. The pocket (now referred to as 160) may include a separate base graft layer stitched or otherwise coupled to the inner layer 22. The base layer 162 may include magnets 163 attached thereto, similarly as described with magnets 150. A cover layer 164 is securely attached to the proximal end 165 of the base layer or the inner layer 22 (as shown), such as by stitching. The distal end 168 of the cover layer 164 is removably attached to the graft material. For example, the distal end 168 may include the lid magnet 170. The distal end of the base layer 162 may include the rim magnet 172 configured for magnetic attraction and coupling to the lid magnet 170. There is enough length or slack in the cover layer 164 to form the cavity sized to receive the microsystem that is magnetically coupled to the magnets 163. The cover layer may include the reinforcement band that is described herein.

Figure 11A:
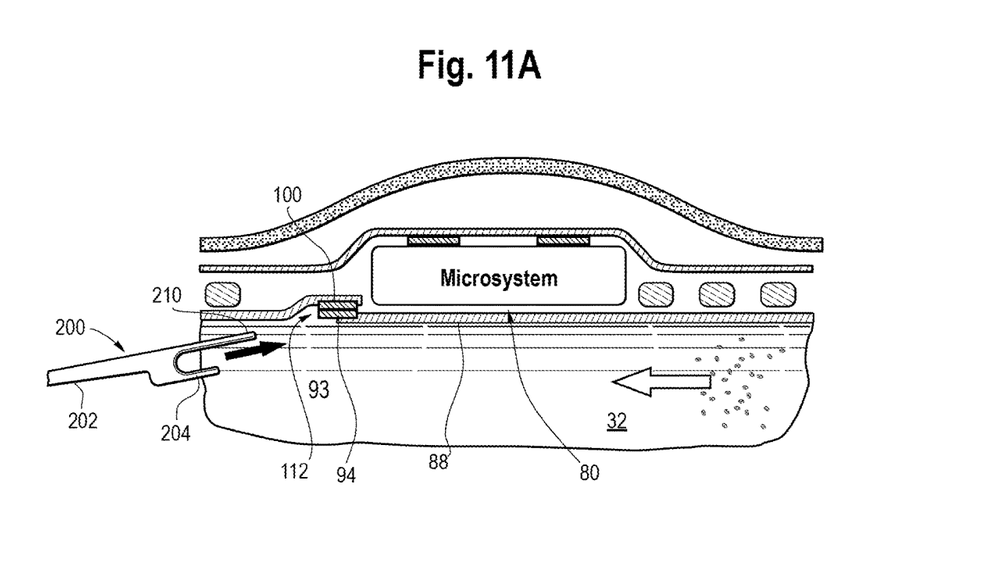
FIGS. 11A-11D depict an example of replacing a microsystem using a pocket configuration of a medical device from inside of the medical device.

FIGS. 11A-11D illustrate a use of the pocket for removing and/or replacing the microsystem in vivo. The microsystem may need removed and/or replaced due to electromechanical failure or software failure, due to a new revision of the microsystem being needed, or when monitoring of the condition is no longer needed. FIG. 11A shows the grasper device 200 having a protruding end 210 configured to removably engage with any one of the grasping features described herein or directly against the flaps and/or lid materials. In one example, access to the body may be attained by inserting an access device, such as an introducer sheath, into the body passageway. One typical procedure for inserting the introducer sheath over an inserted wire guide using the well-known Seldinger percutaneous entry technique. The grasper device 200 may be delivered using the introducer sheath, and advanced to the microsystem M, typically using visual techniques such as fluoroscopy. The grasper device 200 includes an elongated grasper body 202 and a head 204 attached to the grasper body 202. The head 204 includes the protruding end 210. The operator end of the body (not shown) may be manipulated and pushed in order to move the grasper device through the sheath and position the head 204 outside the sheath lumen to couple to the grasping feature of the pocket, such as the grasping feature 112 of the pocket 80.

Figure 11B:
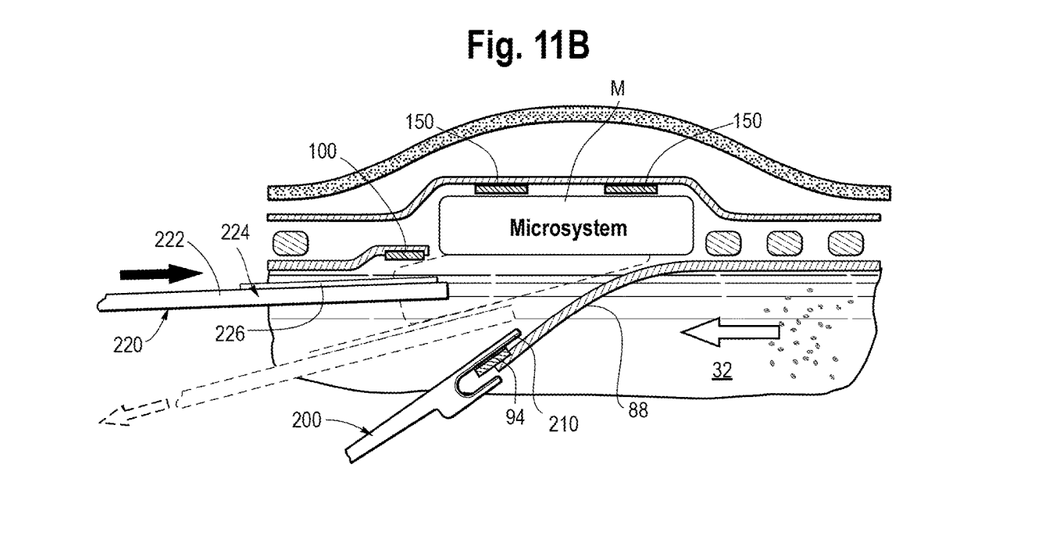
Figure 11C:
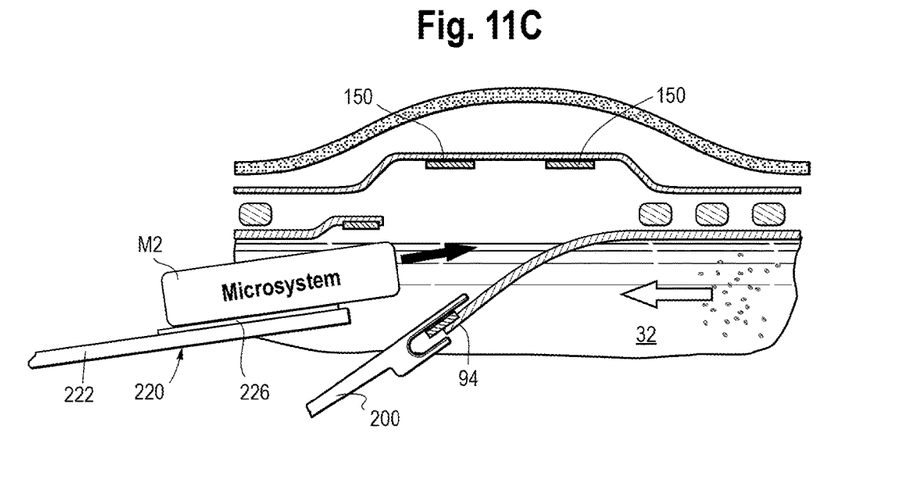

FIG. 11B illustrates the coupling of the protruding end 210 to the grasping feature 112 of the pocket 80. After coupling, the grasper device 200 may be manipulated to break the magnetic coupling between the lid and rim magnets 94, 100 in order to move the lid 88 to the open configuration. Maintaining the lid in the open configuration, a magnetic coupling grasper 220 may be introduced within the same lumen of the introducer sheath and advanced to the microsystem M. The grasper 220 includes an elongated body 222 and a head 224 attached to the body 222. The head 224 includes a magnetic device 226. The operator end of the body (not shown) may be manipulated and pushed in order to move the grasper 220 through the sheath and position the head 224 outside the sheath lumen to couple to the microsystem M. The magnetic device 226 may be configured for selective magnetism. The selective magnetism may occur after the magnetic device 226 clears the rim magnet 100. In another example, a specialized handler pulls the magnet 100 back, for example, in blood flow direction. This may be done in direct contact with the magnet or indirectly by contacting the adjacent cover material of the lid to decouple the magnets 100, 94. Then, the lid can be easily pushed into the open position.

The magnetic devices 226 are coupled to electrical energy via internal wiring or circuits that is coupled to a power conductor, which may be extended through the body 222 to a power supply external to the patient. The selective energization may be controlled by a control switch or there may be switching module (hardware or software) included with the power supply. The magnetic device 226 may include electromagnets that are activated, for example, selectively activated or may be activated to a certain strength to help ensure attachment to the microsystem. The strength capability of the electromagnets is greater than the magnets 150. After the magnetic coupling of the magnetic device 226 and the microsystem M, the grasper 220 may be manipulated to break the magnetic coupling between the microsystem and the magnets 150. After which, the grasper 220 with the microsystem may be withdrawn from the body.

After the microsystem M is removed from the body, the pocket and lid may be closed if no other microsystem is being introduced. On the other hand, a new or second microsystem M2 is oriented and attached to the magnetic device 226 for insertion into the body. The operator end of the body may be manipulated and pushed in order to move the grasper 220 with the second microsystem M2 into position relative to the pocket, as shown FIG. 11C. The second microsystem is positioned within the pocket opening and aligned with the magnets 150. The magnetism of the magnetic device 226 may be weakened in order to allow the magnets 150 to magnetically couple to the second microsystem M2.

Figure 11D:
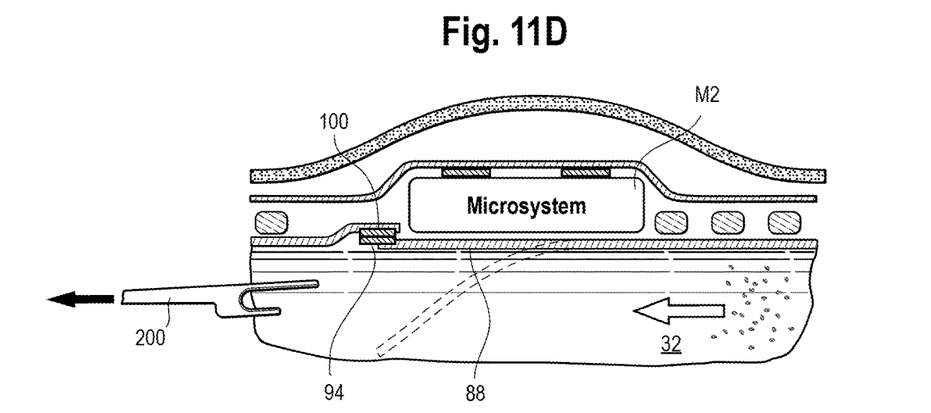

After successful insertion of the microsystem into the pocket, the grasper device 200 may be manipulated to magnetically couple the lid and rim magnets 94, 100 together in order to move the lid 88 to the closed configuration. Thereafter, the protruding end 210 may be decoupled from the grasping feature 112 of the pocket 80, and the grasper device 200 may be withdrawn from the body, such as shown in FIG. 11D.

Similar methods may be utilized with other pocket configurations. For example, for pocket 60, the grasper 200 may be omitted, and the grasper 220 may be utilized for the removal of the microsystem M and the insertion of another microsystem. In another example, for pocket 130, the grasper 200 may be used for removably coupling to the first flap. The grasper 220 may be utilized for the removal of the microsystem M from the pocket 130 when magnets 150 are employed. Other tools may be used to create the opening between the flaps for access to the pocket and for positioning the microsystem in an orientation for removal through the flap opening.

In the figures, the various configurations of pockets are shown disposed along the luminal surface 32 of the graft covering 12. It is contemplated that any one of the pockets may be disposed along the abluminal surface 33 of the graft covering, where the pocket is disposed and accessible from the outside of the graft, which may be beneficial to inserting a microsystem at the bedside of a patient prior to implantation. Such pockets disposed along the abluminal surface 33 may have similar features and components as the pockets shown in the Figures except disposed along the abluminal surface 33 and/or outer layer 20. In another example, a first pocket may be disposed along the luminal surface and a second pocket may be disposed along an abluminal surface.

The magnetic device or magnets may be rare earth magnets or electromagnets having sufficient magnetic power and strength to attract and align another source of magnetic attraction such as the magnets of the other device in-vivo. The magnets may include the neodymiun-iron-boron compositions and cobalt-samarium compositions. Any number of individual magnets (e.g., zero, one, two, three, four, five, six, seven, or eight or more, etc.) may be provided. These magnets may located inside, outside, or combination thereof of the body of the devices, and may be positioned anywhere along the length of the bodies. Each magnet may be fixed in or on the bodies by any suitable method, for example, embedded in, adhered to or friction fit within the bodies. The magnets may have alternating polarity (for example, each magnet may have the opposite polarity as any adjacent magnets), the same polarity, or combinations thereof.

The term "graft" describes an object, device, or structure that is joined or that is capable of being joined to a body part to enhance, repair, or replace a portion or a function of that body part. Grafts that can be used to repair body vessels include, for example, films, coatings, or sheets of material that are formed or adapted to conform to the body vessel that is being enhanced, repaired, or replaced. The graft material may include a biocompatible synthetic or biomaterial. Examples of suitable synthetic materials include fabrics, woven and nonwoven materials, and porous and nonporous sheet materials. Other synthetic graft materials include biocompatible materials such as polyester, polytetrafluoroethylene ("PTFE"), polyurethane ("PU"), fluorinated ethylene propylene ("FEP") and the like. The materials may be elestrospun from polymer fibers, such as PTFE fibers, to form the graft layers. Examples of suitable biocompatible materials include, for example, pericardial tissue and extracellular matrix materials ("ECMM") such as SIS.

Other synthetic materials, such as biocompatible synthetic materials, may be used for the graft material. Synthetic materials may include polymers such as, for example, poly (urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly (methacrylic acid), polylactides ("PLA"), polyglycolides ("PGA"), poly(lactide-co-glycolid-es) ("PLGA"), polyanhydrides, polyorthoesters or any other similar synthetic polymers that may be developed that are biocompatible. Biocompatible synthetic polymers also may include copolymers, blends, or any other combinations of the forgoing materials either together or with other polymers generally. The use of these polymers will depend on given applications and specifications required. Suitable polymer material may include, for example, polyester such as DACRON™, polyetherurethanes such as THORALON® from Thoratec Corporation (Pleasanton, Calif.), or polyethylene terephthalate ("PET").

In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a porous sheet can be used to make a graft material, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above. The porous sheet may be made of one or more polymers that do not require treatment or modification to be biocompatible.

The graft material, the coating, or one class of materials for electrospinning may also include extracellular matrix materials. The "extracellular matrix" is typically a collagen-rich substance that is found in between cells in animal tissue and serves as a structural element in tissues. Such an extracellular matrix is preferably a complex mixture of polysaccharides and proteins secreted by cells. The extracellular matrix can be isolated and treated in a variety of ways. Following isolation and treatment, it is referred to as an "extracellular matrix material," or ECMM. ECMMs may be isolated from submucosa (including small intestine submucosa), stomach submucosa, urinary bladder submucosa, tissue mucosa, renal capsule, dura mater, liver basement membrane, pericardium or other tissues.

Stent frame structure may include any suitable biocompatible material, including, but not limited to fabrics, metals, plastics, and the like. Examples of suitable materials include metals such as stainless steel and nitinol, and plastics such as PET, PTFE and polyurethane. The stent frame structure may be "expandable," that is, it may be capable of being expanded to a larger-dimension configuration. In one example, the stent frame structure may have one or more self-expanding portions and one or more balloon-expandable portions. In one example, the stent structure may be a zigzag stent. The stent struts that are interconnected to one another represents specific configurations of a wire member that comprises a basic structural component of the stent. As used herein, the term "wire" refers to any filamentary member, including, but not limited to, drawn wire and filaments that have been laser cut from a cannula. The shape, size, and dimensions of the stent structure may vary. The size of these components and the overall stent structure is determined primarily by the diameter of the vessel lumen at the intended implant site, as well as the desired length of the overall stent device. The stent structure and/or ring structures may have a common cross-sectional area along the body or may vary to have different cross-sectional areas. The reinforcement bands or edge bands described herein may be made of any one or more of the stent materials.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. An implantable medical device comprising:
a tubular graft material having an abluminal surface and a luminal surface,
a pocket disposed along at least one of the luminal and abluminal surfaces of the graft material, the pocket including a pocket opening leading into an enclosed cavity, the enclosed cavity of the pocket sized to receive at least a portion of a microsystem, wherein the microsystem collects information, and wherein the pocket has an open state for retrieval of the microsystem.

2. The device of claim 1, wherein the pocket is disposed along the luminal surface of the graft material.

3. The device of claim 2, wherein the pocket includes a lid having a base extended from or coupled to the graft material and a lid tip disposed downstream of the base, the lid pivotable about the base between an open configuration and a closed configuration, wherein the lid tip is removably attached to the graft material with a coupling device.

4. The device of claim 3, wherein the lid includes a reinforcement band.

5. The device of claim 3, wherein the coupling device includes a lid magnet and a rim magnet, the lid magnet is coupled to the lid, and the rim magnet coupled to a pocket edge of the pocket, the rim magnet configured to magnetically couple to the lid magnet when the lid is in the closed configuration.

6. The device of claim 5, wherein the lid magnet extends beyond an edge of the lid tip and includes a grasping feature accessible outside the lid.

7. The device of claim 1, wherein a reinforcement edge band is disposed about a pocket edge that defines the pocket.

8. The device of claim 1, wherein the pocket includes a magnet to couple to the microsystem when disposed within the pocket.

9. The device of claim 8, wherein the microsystem is removably attached within the pocket.

10. The device of claim 1, further comprising a second pocket disposed along the graft material.

11. The device of claim 1, wherein the pocket is defined by a cover graft layer having a proximal end securely attached to the graft material and a distal end removably attached to the graft material.

12. An implantable medical device comprising:
a tubular graft material having an abluminal surface and a luminal surface,
a pocket disposed along at least one of the luminal and abluminal surfaces of the graft material, the pocket including a pocket opening leading into an enclosed cavity, the enclosed cavity of the pocket sized to receive at least a portion of a microsystem, wherein the pocket is accessible in vivo for removal of the microsystem from the pocket,
wherein the pocket includes a lid having a base extended from or coupled to the graft material and a lid tip disposed downstream of the base, the lid pivotable about the base between an open configuration and a closed configuration, wherein the lid tip is removably attached to the graft material with a coupling device; and
a grasping feature that extends beyond the lid tip.

13. The device of claim 12, wherein the microsystem collects information.

14. The device of claim 12, wherein the pocket has an open state for retrieval of the microsystem.

15. An implantable medical device comprising:
a tubular graft material having an abluminal surface and a luminal surface,
a pocket disposed along at least one of the luminal and abluminal surfaces of the graft material, the pocket including a pocket opening leading into an enclosed cavity, the enclosed cavity of the pocket sized to receive at least a portion of a microsystem, wherein the pocket is accessible in vivo for removal of the microsystem from the pocket,
wherein the pocket includes a lid having a base extended from or coupled to the graft material and a lid tip disposed downstream of the base, the lid pivotable about the base between an open configuration and a closed configuration, wherein the lid tip is removably attached to the graft material with a coupling device; and a grasping feature that comprises one of a radial lip, an indentation, an opening or a slot.

16. The device of claim 15, wherein the microsystem collects information.

17. The device of claim 15, wherein the pocket has an open state for retrieval of the microsystem.

* * * * *